United States Patent [19]

Hetzel et al.

[11] 4,147,714
[45] Apr. 3, 1979

[54] PROCESS FOR THE PREPARATION OF POLYISOCYANATES WHICH CONTAIN BIURET GROUPS

[75] Inventors: Hartmut Hetzel, Cologne; Klaus König, Leverkusen; Hans G. Schmelzer, Stommeln; Kuno Wagner, Leverkusen, all of Fed. Rep. of Germany

[73] Assignee: Bayer Aktiengesellschaft, Leverkusen, Fed. Rep. of Germany

[21] Appl. No.: 905,245

[22] Filed: May 12, 1978

Related U.S. Application Data

[63] Continuation of Ser. No. 771,292, Feb. 23, 1977, abandoned.

[30] Foreign Application Priority Data

Mar. 10, 1976 [DE] Fed. Rep. of Germany ....... 2609995

[51] Int. Cl.² .......................................... C07C 127/24
[52] U.S. Cl. ............................................. 260/453 AB
[58] Field of Search ................................. 260/453 AB

[56] References Cited

U.S. PATENT DOCUMENTS

| 3,903,126 | 9/1975 | Woerner et al. | 260/453 AB |
| 3,903,127 | 9/1975 | Wagner et al. | 260/453 AB |

FOREIGN PATENT DOCUMENTS

1263609 2/1972 United Kingdom.

*Primary Examiner*—Dolph H. Torrence
*Attorney, Agent, or Firm*—Gene Harsh; Lawrence S. Pope; Frederick H. Colen

[57] ABSTRACT

This invention relates to an improved process for the preparation of polyisocyanates which contain biuret groups by the direct reaction of polyamines in vapor form with polyisocyanates.

7 Claims, No Drawings

PROCESS FOR THE PREPARATION OF POLYISOCYANATES WHICH CONTAIN BIURET GROUPS

This is a continuation of application Ser. No. 771,292 filed Feb. 23, 1977 and now abandoned.

BACKGROUND OF THE INVENTION

It is already known, for example, to prepare polyisocyanates containing biuret groups from diisocyanates and water (U.S. Pat. No. 3,201,372); hydrogen sulphide (British Pat. No. 1,043,672); formic acid (U.S. Pat. No. 3,392,183) or tertiary alcohols (U.S. Pat. No. 3,358,010). In these processes, some of the isocyanate groups of the diisocyanates are converted into amino groups which then react with excess diisocyanate to form biuret polyisocyanates via the corresponding urea diisocyanates.

These prior art processes have various disadvantages. Firstly, the heterogeneous reaction of diisocyanates with water involves the risk of formation of insoluble polyureas which are difficult to remove. Furthermore, the above mentioned process invariably produce gaseous by-products such as carbon dioxide, carbon monoxide, carbon sulphoxide or olefines. Lastly, a particularly serious disadvantage of these prior art processes is that some of the isocyanate groups in the diisocyanate used as starting material are inevitably destroyed by amine formation. There have, therefore, been several attempts to provide a process for the production of polyisocyanates which contain biuret groups by the direct reaction of polyamines with polyisocyanates, without liberation of volatile by-products or destruction of isocyanate groups by amine formation. Because of the vigorous reaction of amino groups with isocyanate groups, however, considerable practical difficulties were encountered because of the very copious production of insoluble polyureas and crosslinked products. The only methods which met with some measure of success were, therefore, those in which very special starting materials were used. Thus, according to U.S. Pat. No. 3,441,588, higher molecular weight diaminopolyethers must be used, as the diamine component in order to prevent the formation of the above mentioned difficulty soluble by-products. It is clear that a process requiring the previous complicated preparation of diamino polyethers cannot be regarded as a commercially completely satisfactory solution to the problem. The process according to U.S. Pat. No. 3,824,266 is restricted to the use of diprimary aromatic diamines whose reactivity is reduced by steric or electronic effects and also does not provide a commercially acceptable method of producing polyisocyanates with biuret groups.

The process according to U.S. Pat. No. 3,903,126 also does not provide a commercially acceptable method of producing polyisocyanates with biuret groups by the direct reaction of organic polyisocyanates with simple aliphatic and/or cycloaliphatic polyamines. Thus, according to Example 16 of U.S. Pat. No. 3,903,126 preparation of polyisocyanates with biuret groups from hexamethylene diisocyanate and hexamethylene diamine requires reheating of the reaction mixture to about 180° C. for about 12 hours in order to complete the reaction. Such long reheating at a high temperature is not only uneconomical, particularly under large scale production conditions, but also leads to discoloration of the reaction product so that its use in lightfast lacquers is very restricted. Moreover, when Example 16 of U.S. Pat. No. 3,903,126 was repeated, it was found that it was impossible by this method to obtain a biuret polyisocyanate which was both free from monomeric diisocyanate used as starting material and completely free from insoluble gel-like by-products.

SUMMARY OF THE INVENTION

It has now surprisingly been found that simple aliphatic and/or cycloaliphatic polyamines can be directly reacted with organic polyisocyanates to yield the corresponding biuret polyisocyanates if the biuret-free polyisocyanate used as starting material is first placed into the reaction vessel and the polyamine is then introduced in the gaseous form. Under these conditions, the reaction mixture remains a clear solution throughout the introduction of polyamine even when hexamethylene diisocyanate is reacted with hexamethylene diamine, and the reaction is completed as soon as all the diamine has been introduced so that no reheating is necessary.

The present invention thus relates to a process for the preparation of biuret polyisocyanates by reaction of organic polyamines which have two aliphatically and/or cycloaliphatically bound primary amino groups with organic polyisocyanates which are free from biuret groups at a molar ratio of amino groups to isocyanate groups of between about 1:5 and 1:100, characterized in that the polyamines are reacted in vapor form with the polyisocyanates which have been heated to a temperature of from about 100° C. to 250° C.

DETAILED DESCRIPTION OF THE INVENTION

Organic polyamines having two aliphatically or cycloaliphatically bound primary amino groups are used for the process according to the invention. Examples of such polyamines are diprimary diamines of the formula $R(NH_2)_2$ in which R represents an aliphatic hydrocarbon group with 2 to 12 carbon atoms, a cycloaliphatic hydrocarbon group with 4 to 7 carbon atoms or an araliphatic hydrocarbon group with 8 to 10 carbon atoms e.g. ethylene diamine; propylene-1,2- and -1,3-diamine; 1,4-diaminobutane; 2,2-dimethylpropane-1,3-diamine; 1,6-diaminohexane; 2,5-dimethylhexane-2,5-diamine; 2,2,4-trimethylhexane-1,6-diamine; 1,8-diaminooctane; 1,10-diaminodecane; 1,11-undecanediamine; 1,12-dodecanediamine; 1-methyl-4-(aminoisopropyl)-cyclohexylamine-(1); 3-aminomethyl-3,5,5-trimethyl-cyclohexylamine-(1); 1,2-bis-(aminomethyl)-cyclobutane; p-xylylenediamine; 1,4-bis-(2-aminoethyl)-benzene; 1,2- and 1,4-diaminocyclohexane; 1,2-, 1,4- and 1,8-diaminodecaline; 1-methyl-4-aminoisopropyl-cyclohexylamine-(1); 4,4'-diamino-dicyclohexyl; 4,4'-diamino-dicyclohexylmethane; 2,2'-(bis-4-aminocyclohexyl)-propane; 3,3'-dimethyl-4,4'-diamino-dicyclohexylmethane; 1,2-bis-(4-aminocyclohexyl)-ethane and 3,3',5,5'-tetramethyl-bis-(4-aminocyclohexyl)-methane and -propane.

Other suitable polyamines for the process according to the invention include bis-(aminoalkyl)-amines preferably having a total of from 4 to 12 carbon atoms, e.g. bis-(2-aminoethyl)-amine, bis(3-aminopropyl)-amine, bis-(4-aminobutyl)-amine, bis-(6-aminohexyl)-amine and isomeric mixtures of dipropylene triamine and dibutylene triamine.

The preferred diamines are tetramethylene diamine, hexamethylenediamine and 1,2-bis-(aminomethyl)-cyclobutane, particularly hexamethylenediamine.

Suitable polyisocyanates for the process according to the invention are in particular diisocyanates of the formula Q(NCO)$_2$ in which Q represents an aromatic hydrocarbon group with 6 to 15 carbon atoms; an araliphatic hydrocarbon group with 8 to 10, preferably 8, carbon atoms; an aliphatic hydrocarbon group with 4 to 12 carbon atoms or a cycloaliphatic hydrocarbon group with 4 to 15 carbon atoms. Examples include tolylene-2,4- and -2,6-diisocyanates and their isomeric mixtures; 4,4'- and 2,4'-diphenylmethane diisocyanate and xylylene diisocyanate. Particularly suitable are the aliphatic and cycloaliphatic diisocyanates such as 1,4-diisocyanatobutane; 1,6-diisocyanatohexane; 2,4,4-trimethylhexane-1,6-diisocyanate; 1,11-diisocyanatoundecane; 3-isocyanatomethyl-3,5,5-trimethyl-cyclohexylisocyanate-(1); 1,4-cyclohexane diisocyanate; 4,4'-dicyclohexylmethane diisocyanate and 1,2-bis-(isocyanatomethyl)-cyclobutane. Hexamethylene diisocyanate is particularly preferred.

Products which are particularly light in color are obtained by the process according to the invention if the diisocyanate used as a starting material is preheated for several hours, suitably about 6 to 10 hours, at about 120° to 195° C., preferably about 160° to 180° C., and then distilled.

The process according to the invention is preferably carried out by introducing the diisocyanate into the reaction vessel at an excess of about 5 to 100 and preferably 7 to 25 isocyanate group to one primary amino group at elevated temperature with vigorous stirring and adding the polyamine in gaseous form, optionally at reduced pressure, and if desired together with a stream of inert gas. In cases where the polyamine has a lower boiling point than the diisocyanate, the polyamine vapor can be introduced through a simple inlet tube dipping into the diisocyanate. A suitable evaporator for the polyamine is attached to the inlet tube and a vacuum must be applied to keep the reactor at a pressure at which the boiling point of the polyamine is about 10° to 80° C. below the temperature of the diisocyanate in the reaction vessel because otherwise the polyamine will partly condense in the inlet tube and come into contact with the diisocyanate as a liquid, hence leading to the formation of solid polyureas and blockage of the inlet tube. If, especially in the case of large reaction batches, the column of liquid above the outlet point of the polyamine vapor is so high that its hydrostatic pressure raises the boiling point of the polyamine to a temperature close to the temperature of the diisocyanate, it is preferable to use a hollow stirrer (gasification stirrer) for introducing the polyamine vapor. This stirrer will exert additional suction and ensure uniform distribution of the polyamine vapor in the diisocyanate.

If the boiling point of the polyamine is above that of the diisocyanate, the inlet tube for introducing the polyamine vapor must be heatable to temperatures above that of the diisocyanate in the vessel. In that case, the inlet tube is preferably heat insulated on the outside to prevent excessive heat exchange with the diisocyanate.

When carrying out the process on a commercial scale, the inlet tube may be replaced not only by a hollow stirrer as already mentioned above, but also by an annular nozzle, which may be one which closes mechanically.

There are two methods, for example, by which the rate of introduction of polyamine vapor may be controlled. In the first of these, the total quantity of polyamine is introduced into the evaporator and the rate of distillation is controlled by the supply of heat. In the second, the rate of introduction of polyamine into the overheated evaporator is controlled.

It is clear that the process may also be carried out continuously. In that case, a quantity of diisocyanate suitable for the rate of addition of polyamine is introduced into the reactor and an appropriate proportion of the reaction mixture is continuously removed, if desired through an overflow.

The temperature of the diisocyanate in the reaction vessel is chosen so that the $\alpha,\omega$-diisocyanato- or bis- or tris-urea compounds originally formed from the polyamine and diisocyanate rapidly react with addition of isocyanate groups to the urea groups to form biuret compounds in order to avoid precipitation of the difficulty soluble and in most cases high melting urea compounds. It has in practice been found that temperatures above 100° C. are required for this purpose and temperatures above 120° C. are preferable. The upper limit to the temperature range is given by the tendency to discoloration and side reactions and is a maximum of 250° C. The preferred temperature range is from about 130° C. to 200° C., particularly from about 140° C. to 180° C.

In a particular embodiment of the process according to the invention by which exceptionally low viscosity biuret polyisocyanates can be prepared, the gaseous polyamine is introduced into the diisocyanate together with a gas which is inert with the reactants and with the end products under the reaction conditions. Nitrogen, for example, is a suitable carrier gas for this purpose. In this embodiment of the process, the volumetric ratio of carrier gas to polyamine vapor is generally between about 2:1 and 100:1, preferably between about 40:1 and 80:1.

The polyamine vapor can, of course, be obtained not only by evaporating a liquid polyamine but also by sublimation of a solid polyamine or simply by passing a vigorous stream of inert gas through a liquid polyamine, a mixture of polyamine vapor and polyamine aerosol being obtained in the last mentioned case.

When the process according to the invention is carried out under the given temperature conditions, the reaction to the biuret polyisocyanate is spontaneous so that virtually no reheating is required once all the polyamine has been added. At the same time, continuous decomposition and reformation of biuret groups equilibrates the reaction mixture to a complex mixture of mono-, bis- and tris-biurets and higher biurets whose molar distribution finally depends only on the selected isocyanate/amine ratio. Because of these regrouping reactions, a proportion of the polyamine, depending on the selected isocyanate excess, is converted into the corresponding polyisocyanate. A biuret polyisocyanate mixture which has been prepared by the process according to the invention, for example from hexamethylene diisocyanate and 3,3'-dimethyl-4,4'-diamino-dicyclohexylmethane, contains, after removal of unreacted excess of hexamethylenediisocyanate, will contain 3,3'-dimethyl-4,4'diisocyanatodicyclohexylmethane corresponding to the diamine used as starting material, the quantity depending on the isocyanate/amine ratio.

If, for example, 1,4-diaminocyclohexane is used for biuretizing, e.g. 1,6-diisocyanatohexane, then the reaction mixture will contain 1,4-diisocyanato cyclohexane.

If the biuret polyisocyanate is then freed from excess diisocyanate, the distillate obtained is a diisocyanate mixture which must be used again if the process is carried out on a commercial scale. This necessitates separation of the mixture by distillation because if the mixture were used as such it would require a prolonged starting period, in the case of continuous production, or several batches, in the case of discontinuous production, before a product of constant composition could be obtained. For these reasons, it is preferred to use combinations of diisocyanates and diamines of similar constitution or to carry out biuretization of diisocyanates with amines which are converted into polyisocyanates with a very low vapor pressure. The bis-(aminoalkyl)-amines already mentioned above, for example, are amines which satisfy this condition since, as a result of the equilibration reaction mentioned above, the most volatile polyisocyanate components to which they could give rise are the triisocyanates with one urea group which correspond to the polyamine and which are only difficulty volatile, for example, in comparison with hexamethylene diisocyanate.

The biuret polyisocyanates prepared by the process according to the invention, in particular from aliphatic starting compounds, are valuable raw materials for the production of high quality lacquers which are weather resistant and stable to light. For use in this field, the reaction mixtures are normally freed from excees diisocyanate in order to obtain a polyisocyanate with a low vapor pressure. This can be achieved by extraction or by distillation. Distillation may suitably be carried out with a thin layer evaporator.

EXAMPLES

EXAMPLE 1

4620 g (27.5 mol) of 1,6-diisocyanatohexane are introduced at 160° C. with stirring into a 6-liter four-necked flask equipped with reflux condenser, contact thermometer and stirrer. A glass tube is mounted on the remaining neck of the flask and arranged to dip about 8 cm below the level of the liquid. At the lower end, the tube is bent sideways in the direction of rotation of the stirrer and drawn out to a tip of about 2 mm in diameter. A ground glass sleeve into which the bridge of a 500 ml distillation apparatus opens is attached to the upper end. The bridge is heated to 200° C. The distillation apparatus is charged with 290 g (2.5 mol) of 1,6-diaminohexane heated to 60° C., into which a boiling capillary dips. A vacuum of 50 Torr is produced by means of the reflux condenser of the four-necked flask. A gentle stream of nitrogen is passed through the capillary. The distillation flask is then placed into an oil bath which is at a temperature of 180° C. The diamine begins to distill off at a reaction temperature of from 125° C. to 135° C. The overheating vapors in the bridge are immediately absorbed by the diisocyanate. The speed of distillation is regulated by the depth of immersion of the distillation flask in the oil bath so that the reaction is completed in about 2 hours. The clear reaction mixture is then subjected to thin layer distillation at 175° C. and 1 Torr. 2150 g of a pale yellow biuret polyisocyanate having an isocyanate content of 22.3% and a viscosity of 12,000 cP at 25° C. are obtained. Gel chromatographic analysis indicates approximately the following composition:

| | |
|---|---|
| 0.3 % by weight | 1,6-diisocyanatohexane |
| 38.5 % by weight | monobiuret |
| 19.5 % by weight | bis-biuret |
| 12.0 % by weight | tris-biuret |
| 7.8 % by weight | tetra-biuret |
| 5.0 % by weight | penta-biuret |
| 16.9 % by weight | unidentified or higher molecular weight constituents. |

EXAMPLE 2

Using the same apparatus as in Example 1, 2856 g (17 mol) of 1,6-diisocyanatohexane are placed into a 4-liter flask at 180° C. and 232 g (2 mol) of 1,6-diaminohexane are distilled into it at 80 Torr over a period of 60 minutes. The almost completely clear reaction mixture is freed from a small quantity of solid particles by pressure filtration and from excess diisocyanate by thin layer distillation. A viscous, pale yellow biuret polyisocyanate having an isocyanate content of 20.4% and a viscosity of 73,400 cP at 25° C. is obtained.

EXAMPLE 3

1288 g (7 2/3 mol) of 1,6-diisocyanatohexane are introduced into a 2-liter reaction flask at 160° C. and 50 Torr. The distillation apparatus described in Example 1 is completely immersed in an oil bath which is at a temperature of 220° C. The distillation bridge is also heated to 220° C. 38.7 g (⅓ mol) of 1,6-diaminohexane at a temperature of 80° C. are introduced dropwise into the distillation flask from a dropping funnel over a period of 30 minutes, the diaminohexane being rapidly gasified on entering the distillation flask. Thin layer distillation of the clear reaction mixture yields 305 g of a thin liquid consisting of a biuret polyisocyanate having an isocyanate content of 23.8% and a viscosity of 2240 cP at 25° C.

COMPARISON EXAMPLE I 1848 g (11 mol) of 1,6-diisocyanatohexane are introduced into a nitrogen atmosphere at 70° C. 116 g (1 mol) of 1,6-diaminohexane are added dropwise from a heated dropping funnel over a period of about 60 minutes with vigorous stirring. The pasty reaction mixture obtained is heated to 180° C. When stirring is continued for a further 12 hours at this temperature, the resulting brown reaction mixture still contains considerable proportions of gel-like solids which are difficult to remove by filtration.

EXAMPLE 4

1512 g (9 mol) of 1,6-diisocyanatohexane are introduced into a 2-liter four-necked flask at 12 mm and heated to mild reflux (approximately 135° C.). Using the distillation apparatus described in Example 1 (oil bath and bridge heated to 220° C.), 127.5 g (0.75 mol) of 3-aminomethyl-3,5,5-trimethylcyclohexylamine-1 ("isophorone diamine") in the form of vapor pass through the inlet tube into the diisocyanate over a period of 50 minutes and immediately react with the diisocyanate to form a clear product. Thin layer distillation yields 650 g of a light colored biuret polyisocyanate having an isocyanate content of 23.4% and a viscosity of 18,450 cP at 25° C. According to the gas chromatograph, the distillate (990 g) contains 0.69% by weight of 3-isocyanatomethyl-3,5,5-trimethylcyclohexyl isocyanate-(1).

COMPARISON EXAMPLE II 1512 g (9 mol) of 1,6-diisocyanatohexane are placed in the reaction vessel at 25° C. 127.5 g (0.75 mol) of 3-aminomethyl-3,5,5-trimethyl-cyclohexylamine-(1) are introduced dropwise over a period of 20 minutes. A pasty but easily stirrable reaction mixture is obtained. The polyurea is then heated to cause further reaction. The solid constituents coagulate to a rubbery lump at about 140° C. so that stirring cannot be continued. The mixture is then heated to 170° C. for 8 hours without further stirring. By the end of that time, the reaction mixture is to some extent homogeneous. It changes to a deep yellow in the course of this time.

EXAMPLE 5

1680 g (10 mol) of 1,6-diisocyanatohexane are introduced into a reaction vessel under a light vaccum (600 to 650 Torr) at 160° C. 74 g (1 mol) of propylene-1,2-diamine in the form of vapor are then introduced together with a mild stream of nitrogen over a period of 90 minutes through a gasification stirrer with stirrer stem heated to 200° C. A clear reaction product is obtained and subjected to thin layer distillation. The yield is 830 g of the pale yellow biuret polyisocyanate having an isocyanate content of 21.7% and a viscosity of 4800 cP at 25° C.

EXAMPLE 6

1512 g (9 mol) of 1,6-diisocyanatohexane are placed in a reaction vessel at 160° C. and 80 Torr. 43 g (0.377 mol) of 1,4-diaminocyclohexane are then introduced as vapor over a period of 30 minutes as described in Example 3. The crude product is filtered to remove the very few solid particles contained in it and is then subjected to thin layer distillation. 380 g of a thin liquid, almost colorless, biuret polyisocyanate having an isocyanate content of 24.3% and a viscosity of 2400 cP at 25° C. are obtained.

EXAMPLE 7

1512 g (9 mol) of 1,6-diisocyanatohexane are placed in a reaction vessel at 140° C. and 50 Torr. 158 g (1 mol) of 2,2,4-trimethyl-hexane-1,6-diamine in the form of vapor superheated to 200° C. are then introduced through a heatable inlet tube with stirring. After treatment in a thin layer evaporator, the clear reaction mixture yields 870 g of a pale yellow biuret polyisocyanate which has an isocyanate content of 21.1% and a viscosity of 21,700 cP at 25° C.

EXAMPLE 8

1554 g (7 mol) of 3-isocyanatomethyl-3,5,5-trimethyl-cyclohexylisocyanate-(1) are placed in a reaction vessel at 160° C. and 12mm. 170 g (1 mol) of 3-aminomethyl-3,5,5-trimethylcyclohexylamine-(1) in the form of vapor super-heated to 200° C. are introduced over a period of 2 hours as described in Example 1. The clear biuret polyisocyanate solution has an isocyanate content of 27.6% and a viscosity of 7300 cP at 25° C.

EXAMPLE 9

1512 g (9 mol) of 1,6-diisocyanatohexane are placed in a reaction vessel at 160° C. and 50 Torr. 61.8 g (0.6 mol) of bis-(2-aminoethyl)-amine are introduced in vapor form over a period of 40 minutes in a similar manner to Example 1. After thin layer treatment, the clear reaction mixture yields 620 g of a pale yellow biuret polyisocyanate having an isocyanate content of 28.0% and a viscosity of 10,300 cP at 25° C.

EXAMPLE 10

Thin layer treatment of the clear reaction mixture obtained from 1512 g (9 mol) of 1,6-diisocyanatohexane and 984 g (0.75 mol) of di-(1,2-propylene)-triamine (isomeric mixture) in a similar manner to Example 9 yields 680 g of a pale yellow biuret polyisocyanate having an isocyanate content of 20.1% and a viscosity of 23,000 cP at 25° C.

EXAMPLE 11

When 2520 g (15 mol) of 1,6-diisocyanatohexane and 131 g (1 mol) of bis-(3-aminopropyl)-amine are reacted together and freed from excess diisocyanate in a similar manner to Example 9, a pale yellow biuret polyisocyanate having an isocyanate content of 22% and a viscosity of 12,500 cP at 25° C. is obtained.

In Examples 9, 10, 11, 1,6-diisocyanatohexane obtained as distillate from thin layer distillation contains no other isocyanate component.

EXAMPLE 12

1740 g (10 mol) of an isomeric mixture of 80% of 2,4- and 20% of 2,6-tolylenediisocyanate are placed in a reaction vessel at 150° C. and 80 Torr. 158 g (1 mol) of 2,2,4-trimethylhexane-1,6-diamine are then introduced through a heatable tube as vapor superheated to 220° C. in a similar manner to Example 7. A clear yellow biuret-molified polyisocyanate solution having an isocyanate content of 35.7% and a viscosity of 200 cP at 25° C. is obtained.

COMPARISON EXAMPLE III

The following comparison example is carried out in three variations (a), (b), and (c) to demonstrate that the preparation of biuret polyisocyanates by the procedure described in Example 16 of U.S. Pat. No. 3,903,126 is hardly a commercially usable process since the adverse phenomena known from German Pat. No. 1,770,927 are also observed when the method according to this Example is carried out. Considerable difficulties are encountered, particularly when the process is carried out with large batches because large quantities of insoluble polyureas and cross-linked porducts are formed which, although they can be degraded at temperatures of about 200° C., promote the formation of unwanted, heavily colored by-products due to the high thermal stresses on the reaction mixture.

Method (a)

(corresponding to Example 16 of U.S. Pat. No. 3,903,126)

14.5 Parts (0.125 mol) of hexamethylenediamine heated to 70° C. are added over a period of 20 minutes at about 25° C. to 168 parts (1 mol) of hexamethylene-1,6-diisocyanate under a nitrogen atmosphere with stirring. The spontaneous precipitation of the pasty, completely insoluble higher molecular weight α,ω-diisocyanatopolyureas sets in at once. The polyureas cannot be observed to dissolve evenly. To achieve biuretization, which proceeds extremely slowly, the reaction mixture must be stirred at 180° C. for 12 hours, during which time the solution acquires a reddish yellow tinge. The reaction mixture (yield about 182 parts by weight) contains pulverulent constituents and gel particles and about 20% by weight of monomeric hexamethylene diisocyanate. It contains a total of 3.5 parts by weight of higher molecular weight constituents which can only be decomposed very slowly at 200° C. When attempts are made to filter this solution, the filter is blocked by the gel particles. After isolation of the solution by centrifuging and removal of monomers by thin layer distillation, a polyisocyanate mixture containing biuret groups is obtained in the form of a yellow brown product with a red tinge. The product has an isocyanate content of 17.1% and a viscosity of 14,300 cP at 25° C. It is unsuitable for the production of lightfast, high gloss lacquer films which can be cross-linked by moisture.

Method (b)

The procedure is the same as in method (a) but 10 times the quantity of starting materials are used. The time taken for dropwise addition of hexamethylenediamine is 20 minutes. The pasty polyureas cannot be seen to dissolve uniformly. The procedure is otherwise the same as under (a). The reddish yellow brown end product cannot be filtered on account of its substantially higher proportion of pulverulent constituents and gel particles (about 45 parts by weight) than in method (a). In order to obtain a mixture free from gel, the reaction mixture must be centrifuged and then freed from gel constituents by decanting. After removal of monomers by thin layer distillation, the reaction product is deep brown in color.

%NCO: 16.9 $\eta 25°$ C.: >152,000 cP $\eta 75°$ C.: 29,800 cP

Method (c)

This is carried out in the same way as method (b) but the rate of addition of hexamethylene diamine is slowed down by a factor of 10, i.e. hexamethylenediamine is added dropwise over a period of 200 minutes. The procedure is otherwise the same as in (a) and (b). This method (c) again requires extremely long reaction times of at least 12 hours. The same filtration difficulties arise as in method (b). The end product purified by thin layer distillation is not suitable for the production of lightfast, high gloss two-component lacquers by reaction with hydroxyl polyesters. $\eta 75°$ C. = 29,100 cP.

EXAMPLE 13

This example describes variations (a) and (b) of the process according to the invention, according to which hexamethylenediamine is drawn as superheated vapor (about 190° C.) into hexamethylenediisocyanate (1008 parts by weight = 6 mol) which is at a temperature of 165° C. and a vacuum of about 60 Torr through an inlet tube whose upper part (i.e. up to the depth of immersion) is heated to 190° C. The superheated vapor is produced by evaporating 58 parts by weight of hexamethylenediamine (0.5 mol) at about 115° to 120° C. in a small flask (nitrogen capillary). Superheating of the vapors to about 190° C. is carried out in a 20 cm long tube which is heated to about 210° C. The reaction is carried out in a ground glass beaker to which a vigorously cooled reflux condenser and vacuum attachment are connected.

The heatable inlet tube is immersed to a depth of about 6 cm. No formation of difficulty soluble $\alpha,\omega$-diisocyanato polyureas can be observed in the reaction vessel during the whole time of addition of hexamethylenediamine vapor, which is completed in about 90 minutes (variation (a)). The extremely low concentrations of $\alpha,\omega$-diisocyanatoureas and $\alpha,\omega$-diisocyanatopolyureas formed are converted practically in statu nascendi at the chosen temperature of 165° C. to biuret polyisocyanates by equilibration reactions. The completely gel-free reaction mixture can be immediately freed from monomeric hexamethylene diisocyanate by thin layer distillation at 170° C. and 1 Torr without prior cooling. Yield: 415 parts by weight, % NCO 21.9, $\eta 25°$ C. 11,200 cP, yellow color. In this experiment, the molar ratio of hexamethylenediamine to hexamethylenediisocyanate is 12:1.

The product of the process is eminently suitable both for the production of lightfast one-component lacquers which can be cross-linked by moisture and for the production of two-component lacquers with hydroxyl polyesters with elastic, high gloss films being obtained.

Variation (b) is carried out in exactly the same way as described under (a) except that the rate of addition of superheated hexamethylenediamine vapor is slowed down by a factor of about 2 (= 3 hours). When the reaction mixture has been worked up, the viscosity of the biuret polyisocyanate mixture at 25° C. is about 8500 cP. The viscosity of the end products can, therefore, be reduced without any significant damage to the color by reducing the rate of addition of superheated hexamethylenediamine vapors and doubling the reaction time.

EXAMPLE 14

This Example describes two interesting variations of the process according to which light yellow to colorless biuret polyisocyanates differing widely in their viscosities can be produced even at normal pressure by diluting the superheated hexamethylenediamine vapors with a stream of nitrogen so that from about 40 to 80 parts by volume of nitrogen are introduced for each part by volume of hexamethylenediamine vapor introduced into the hexamethylenediisocyanate which is preheated to 158° C. The small quantities of hexamethylenediisocyanate vapors escaping from the reflux condenser are condensed in a cooling trap.

VARIATION (a)

Molar ratio hexamethylenediisocyanate/hexamethylenediamine = 18:1.

1512 Parts by weight of hexamethylenediisocyanate (9 mol) are heated to 158° C. and 58 parts by weight (0.5 mol) of superheated hexamethylenediamine vapor are introduced together with nitrogen into the reaction vessel from Example 13 through an inlet tube heated to 190° C. The nitrogen is introduced into the hexamethylenediamine evaporator which is heated to a temperature of about 115° C. The quantity of nitrogen is adjusted by a gas meter so that the volumetric ratio of nitrogen to hexamethylenediamine in the inlet tube for superheated vapor is about 40:1. The biuret polyisocyanate solution is ready to be worked up as in Example 13 after only two hours.

The yield is 408 parts by weight, % NCO 21.9, $\eta 25°$ C. 5800 cP.

15 Parts by weight of hexamethylenediisocyanate are found to be condensed in the cooling trap attached to the reflux condenser.

VARIATION (b)

Molar ratio of hexamethylenediisocyanate to hexamethylenediamine = 18:1.

The procedure is the same as in Variation (a) of this example except that the volumetric ratio of nitrogen to hexamethylenediamine is adjusted to about 80:1.

A pale yellow solution is obtained after a reaction time of 2 hours and subjected to thin layer distillation. The yield is 407 parts by wieght, % NCO: 22.3.

The viscosity of this biuret polyisocyanate mixture at 25° C. is only 4500 cP. The product obtained by diluting the superheated vapor mixture has therefore a lower viscosity by about 22% than the product obtained in Variation (a).

VARIATION (c)

Molar ratio hexamethylenediisocyanate/hexamethylenediamine = 24:1.

Volumetric ratio nitrogen/hexamethylenediamine = 80:1.

The reaction is carried out using 2016 parts by weight of hexamethylenediisocyanate and 58 parts by weight (0.5 mol) of superheated hexemethylenediamine vapors in a 3-liter beaker equipped with stirrer and heated inlet tube (see Example 13).

The yield after working up and thin layer distillation is 414 parts by weight of yellow biuret polyisocyanate, viscosity 3200 cP at 25° C.

This low viscosity biuret polyisocyanate is very suitable for the production of solvent-free or low solvent one-component and two-component lacquers. The above mentioned variations (a) to (c) of the process may be carried out continuously by freeing the nitrogen leaving the apparatus from small quantities of hexamethylenediisocyanate in a cooling tower and returning it as propellent gas to the hexamethylenediamine evaporator by a gas pressure pump.

EXAMPLE 15

This example describes the preparation of an almost colorless biuret polyisocyanate from hexamethylenediisocyanate and hexamethylenediamine used in a molar ratio of 8:1 and nitrogen used in a molar ratio to hexamethylenediamine of about 40:1, employing exactly the same procedure as described in Example 14, variation (a). A commercial hexamethylenediamine is used which has previously been heated to 180° C. for 8 hours to destroy unknown impurities and catalytically active compounds. Hexamethylenediisocyanate is then purified by distillation. 672 Parts by weight (4 mol) of the distillate and 58 parts by weight of hexamethylenediamine (0.5 mol) are used. The procedure is otherwise the same as in Example 14, variation (a). The reaction vessel is a 1 liter ground glass beaker.

After thin layer distillation, an almost water-clear biuret polyisocyanate mixture is obtained in a yield of 416 parts by weight, % NCO = 21.5. The product of the process has a viscosity at 25° C. of 24,800 cP.

EXAMPLE 16

The procedure is the same as indicated in Example 14 but using the following compounds as diisocyanates and diamines and carrying out the reaction in a 500 cc stirrer flask:

(a) Tetramethylenediisocyanate (140 parts by weight (1 mol)) and 11 parts by weight (0.125 mol) of tetramethylenediamine, molar ratio tetramethylenediisocyanate:tetramethylenediamine = 8:1.

(b) 1,2-Diisocyanatomethyl cyclobutane (166 parts by weight (1 mol)) and 14.2 parts by weight of 1,2-bis-aminomethyl cyclobutane (0.125 mol) in a molar ratio of 1,2-diisocyanatomethyl cyclobutane:1,2-bis-aminomethyl cyclobutane = 8:1.

(c) Cycloaliphatic diisocyanates consisting of an isomeric mixture of about 70% by weight of

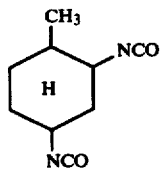

and 30% by weight of

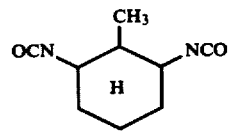

(180 parts by weight = 1 mol) and 15.9 parts by weight (0.125 mol) of a cycloaliphatic diamine consisting of about 70% by weight of

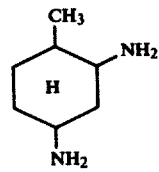

and 30% by weight of

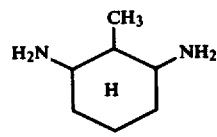

The molar ratio of cycloaliphatic diisocyanate isomers to cycloaliphatic diamine isomers used is 8:1.

The temperatures employed, the rate of addition of superheated diamine/nitrogen vapors and the reaction times are exactly the same as in Example 14, variation (a).

Gel-free solutions of biuret polyisocyanates in excess monomeric diisocyanates are obtained in the following yields:

(a) 150 parts by weight; isocyanate content of gel-free biuret polyisocyanate solution in monomeric diisocyanate: 41.5%

(b) 179 parts by weight; isocyanate content of gel-free biuret polyisocyanate solution in monomeric diisocyanate: 36.6%.

(c) 195 parts by weight; isocyanate content of gel-free biuret polyisocyanate solution in monomeric diisocyanate: 31.5%.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of polyisocyanates having biuret groups by the reaction of aliphatic diamines containing from 2 to 12 carbon atoms with aliphatic diisocyanates containing from 4 to 12 carbon atoms which are free from biuret groups at a molar ratio of $NH_2/NCO$ between about 1:5 and 1:100, characterized in that the diamines are reacted in vapor form with the diisocyanates which are heated to a temperature from about 100° C. to 250° C.

2. A process according to claim 1, characterized in that a gaseous mixture comprising a carrier gas which is inert towards the reactants and the polyamine in vapor form is introduced into the heated polyisocyanates at a volumetric ratio of carrier gas to polyamine of between about 2:1 and 100:1.

3. A process according to claim 1, characterized in that before the biuret-free polyisocyanate is used, it is preheated at about 120° to 195° C. and is then distilled.

4. The process of claim 3 wherein the biuret-free polyisocyanate is preheated for about 6 to 10 hours at about 160° to 180° C. and is then distilled.

5. The process of claim 1 wherein the polyisocyanates are heated to a temperature of from about 130° to 200° C.

6. In a process for the preparation of polyisocyanates having biuret groups by the reaction of aliphatic diamines containing from 2 to 12 carbon atoms with aliphatic diisocyanates containing 4 to 12 carbon atoms which are free from biuret groups at a molar ratio of $NH_2/NCO$ between about 1:5 and 1:100, the improvement comprising reacting the diamines in vapor form with the diisocyanates which are at a temperature at from about 100° to 250° C.

7. A process for the preparation of polyisocyanates having biuret groups by the reaction of hexamethylene diamine with hexamethylene diisocyanate at a molar ratio of $NH_2/NCO$ between about 1:5 and 1:100, characterized in that the hexamethylene diamine is reacted in vapor form with the hexamethylene diisocyanate.

* * * * *